United States Patent
Zhou et al.

(10) Patent No.: US 10,017,585 B2
(45) Date of Patent: Jul. 10, 2018

(54) METHODS AND COMPOSITIONS FOR PROMOTING HAIR GROWTH

(75) Inventors: He Zhou, Beijing (CN); Edward Cochran, Marshfield, MA (US)

(73) Assignee: Momenta Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 13/704,575

(22) PCT Filed: Jun. 15, 2011

(86) PCT No.: PCT/US2011/040470
§ 371 (c)(1),
(2), (4) Date: Apr. 1, 2013

(87) PCT Pub. No.: WO2011/159770
PCT Pub. Date: Dec. 22, 2011

(65) Prior Publication Data
US 2013/0183254 A1 Jul. 18, 2013

Related U.S. Application Data

(60) Provisional application No. 61/355,610, filed on Jun. 17, 2010.

(51) Int. Cl.
| | |
|---|---|
| *C08B 37/10* | (2006.01) |
| *A61K 31/00* | (2006.01) |
| *A61Q 7/00* | (2006.01) |
| *C08B 37/00* | (2006.01) |
| *A61K 8/73* | (2006.01) |
| *A61K 31/337* | (2006.01) |
| *A61K 31/506* | (2006.01) |
| *A61K 31/58* | (2006.01) |
| *A61K 31/727* | (2006.01) |
| *A61K 45/06* | (2006.01) |

(52) U.S. Cl.
CPC .......... *C08B 37/0078* (2013.01); *A61K 8/735* (2013.01); *A61K 31/337* (2013.01); *A61K 31/506* (2013.01); *A61K 31/58* (2013.01); *A61K 31/727* (2013.01); *A61K 45/06* (2013.01); *A61Q 7/00* (2013.01)

(58) Field of Classification Search
CPC ........ A61K 31/727; A61K 31/00; A61Q 7/00; C08B 37/0078; C08B 37/0075
See application file for complete search history.

(56) References Cited

U.S. PATENT DOCUMENTS

| | | |
|---|---|---|
| 3,118,816 A | 1/1964 | Gushing et al. |
| 4,235,871 A | 11/1980 | Papahadjopoulos et al. |
| 4,303,651 A | 12/1981 | Lindahl et al. |
| 4,629,699 A | 12/1986 | Bianchini |
| 4,717,719 A | 1/1988 | Sportoletii et al. |
| 4,727,063 A | 2/1988 | Naggi et al. |
| 4,847,338 A | 7/1989 | Linhardt et al. |
| 4,868,103 A | 9/1989 | Stavrianopoulos et al. |
| 4,916,219 A | 4/1990 | Linhardt et al. |
| 4,990,502 A | 2/1991 | Lormeau et al. |
| 5,262,403 A | 11/1993 | Nicolson et al. |
| 5,264,425 A | 11/1993 | Dal Pozzo et al. |
| 5,296,471 A | 3/1994 | Holme et al. |
| 5,403,827 A | 4/1995 | De-Ambrosi |
| 5,541,166 A | 7/1996 | Parish et al. |
| 5,583,121 A | 12/1996 | Chaudry et al. |
| 5,668,116 A | 9/1997 | Cullis-Hill et al. |
| 5,668,118 A | 9/1997 | Kennedy |
| 5,690,910 A | 11/1997 | Ahmed et al. |
| 5,696,100 A | 12/1997 | Holme et al. |
| 5,707,974 A | 1/1998 | Kennedy |
| 5,733,893 A | 3/1998 | Ornitz |
| 5,763,421 A | 6/1998 | Caretto et al. |
| 5,767,269 A | 6/1998 | Hirsh et al. |
| 5,795,875 A | 8/1998 | Holme et al. |
| 5,808,021 A | 9/1998 | Holme et al. |
| 5,912,237 A | 6/1999 | Kennedy |
| 5,990,097 A | 11/1999 | Kennedy |
| 6,001,820 A | 12/1999 | Hirsh et al. |
| 6,077,683 A | 6/2000 | Kennedy |
| 6,127,347 A | 10/2000 | Chaudry et al. |
| 6,130,210 A | 10/2000 | Caretto et al. |
| 6,150,342 A | 11/2000 | Mattsson et al. |
| 6,545,136 B1 | 4/2003 | Hara et al. |
| 6,596,705 B1 | 7/2003 | Varki et al. |
| 7,781,416 B2 | 8/2010 | Casu et al. |
| 7,790,700 B2 | 9/2010 | Casu et al. |
| 8,067,555 B2 | 11/2011 | Casu et al. |
| 8,071,569 B2 | 12/2011 | Mousa |

(Continued)

FOREIGN PATENT DOCUMENTS

| | | |
|---|---|---|
| BE | 620906 | 11/1962 |
| CN | 1060599 A | 4/1992 |

(Continued)

OTHER PUBLICATIONS

Apsner et al. Dalteparin-induced alopecia in hemodialysis patients: reversal by regional citrate anticoagulation as an example. Blood May 1, 2001 vol. 97(9):2914-2915.*
Gray et al. "Heparin and low-molecular-weight heparin". Thromb Haemost 2008; 99: 807-818.*
Casu et al., "Chemical Derivatization as a Strategy to Study Structure-Activity Relationships of Glycosaminoglycans", Seminars in Thrombosis and Hemostasis, Col. 28, No. 4, pp. 335-342 (2002).
Casu et al., "Non-Anticoagulant Heparins and Inhibition of Cancer", Pathophysiol Haemost Thromb., vol. 36, pp. (2007) 195-203.
Casu et al., "Retention of Antilipemic Activity by Periodate-oxidized Non-anticoagulant Heparins", Arseneimittel Forschung/Drug. Res. vol. 36 (1), No. 4, pp. 637-642 (1986).

(Continued)

*Primary Examiner* — Robert A Wax
*Assistant Examiner* — Olga V Tcherkasskaya
(74) *Attorney, Agent, or Firm* — Brenda Herschbach Jarrell; Rolando Medina; Nishat A. Shaikh

(57) ABSTRACT

Methods and compositions related to promoting hair growth are described.

38 Claims, 1 Drawing Sheet

(56) References Cited

U.S. PATENT DOCUMENTS

| | | | |
|---|---|---|---|
| 8,569,262 | B2 | 10/2013 | Sundaram et al. |
| 8,592,393 | B2 | 11/2013 | Sundaram et al. |
| 2003/0013682 | A1 | 1/2003 | Banito et al. |
| 2003/0147848 | A1 | 8/2003 | Geng |
| 2004/0056249 | A1 | 3/2004 | Russell et al. |
| 2004/0087544 | A1 | 5/2004 | Russo et al. |
| 2005/0107331 | A1 | 5/2005 | Banito et al. |
| 2005/0137167 | A1 | 6/2005 | Casu et al. |
| 2005/0222084 | A1 | 10/2005 | Casu et al. |
| 2005/0282775 | A1 | 12/2005 | Kennedy |
| 2006/0040896 | A1 | 2/2006 | Kennedy |
| 2006/0172968 | A1 | 8/2006 | Casu et al. |
| 2007/0037814 | A1 | 2/2007 | Rawson et al. |
| 2007/0142323 | A1 | 6/2007 | Viskov et al. |
| 2008/0051567 | A1 | 2/2008 | Casu et al. |
| 2008/0280819 | A1* | 11/2008 | Mulugeta et al. ............ 514/9 |
| 2009/0012165 | A1 | 1/2009 | Ueno |
| 2009/0149424 | A1 | 6/2009 | Byun et al. |
| 2010/0021416 | A1 | 1/2010 | Lichter et al. |
| 2010/0081629 | A1 | 4/2010 | Viskov et al. |
| 2010/0316640 | A1* | 12/2010 | Sundaram et al. ...... 424/133.1 |
| 2010/0331746 | A1 | 12/2010 | Deslandes |
| 2011/0076729 | A1 | 3/2011 | Mamuwala et al. |
| 2011/0207919 | A1 | 8/2011 | Beccati et al. |
| 2011/0288046 | A1 | 11/2011 | Venkataraman et al. |

FOREIGN PATENT DOCUMENTS

| | | |
|---|---|---|
| EP | 0121067 A1 | 10/1984 |
| EP | 0140781 A2 | 5/1985 |
| EP | 0346810 A2 | 12/1989 |
| EP | 0557887 A2 | 9/1993 |
| EP | 0735050 B1 | 10/1996 |
| EP | 1129718 A2 | 9/2001 |
| EP | 1268558 A1 | 1/2003 |
| JP | 60115525 | 6/1985 |
| JP | 2002-501613 A | 1/2002 |
| JP | 2006501815 A | 1/2006 |
| JP | 2007-517771 A | 7/2007 |
| JP | 2008150441 A * | 7/2008 |
| JP | 2009538386 A | 11/2009 |
| JP | 2010532314 A | 10/2010 |
| JP | 2011506420 A | 3/2011 |
| WO | 9012561 A1 | 11/1990 |
| WO | 199201003 A1 | 1/1992 |
| WO | 199202232 A1 | 2/1992 |
| WO | 199217187 A1 | 10/1992 |
| WO | 199217188 A1 | 10/1992 |
| WO | 199218545 A1 | 10/1992 |
| WO | 199629973 A2 | 10/1996 |
| WO | 9842865 A1 | 10/1998 |
| WO | 200155221 A1 | 8/2001 |
| WO | 2002083086 A1 | 10/2002 |
| WO | 2003022291 A1 | 3/2003 |
| WO | 2005032483 A2 | 4/2005 |
| WO | 200701409 A2 | 1/2007 |
| WO | 2007014049 A2 | 2/2007 |
| WO | 2007056218 A2 | 5/2007 |
| WO | 2007059313 A1 | 5/2007 |
| WO | 2007144144 A1 | 12/2007 |
| WO | 2009007224 A1 | 1/2009 |
| WO | 2009059283 A1 | 5/2009 |
| WO | WO 2009059283 A1 * | 5/2009 |
| WO | 2011130572 A1 | 10/2011 |

OTHER PUBLICATIONS

Casu et al., "Short Heparin Sequences Spaced by Glycol-Split Uronate Residues Are Antagonists of Fibroblast Growth Factor 2 and Angiogenesis Inhibitors", Biochemistry, vol. 41, pp. 10519-10528 (2002).

Casu et al., "Undersulfated and Glycol-Split Heparins Endowed with Antiangiogenic Activity", J. Med. Chem., vol. 47, pp. 838-848 (2004).

Extended European Search Report from European Application No., 11769624.5 dated Jun. 26, 2013.

Fransson et al., "Relationship between anticoagulant activity of heparin and susceptibility to periodate oxidation", Department of Physiological Chemsitry, vol. 97, No. 1, pp. 119-123 (1979).

Goodman and Gilman's, "The Pharmacological Basis of Therapeutics" published by the McGraw-Hill Companies, Inc. pp. 5-8, 2001.

He Zhou et al., "M-ONC 402-a non anticoagulant low molecular weight heparin inhibits tumor metastasisHe", Proceedings of the American Association for Cancer Research Annual Meeting, p. 69 (2009).

Hrivocíni, et al., "Active Conformation of Glycosaminoglycans. NMR Determination of the Conformation of Heparin Sequences Complexed with Antithrombin and Fibroblast Growth Factors in Solution", Seminars in Thrombosis and Hemostasis, vol. 28, No. 4, pp. 325-333 (2002).

Icli et al., "Low moelecular weight heparin (LMWH) increase the efficacy of cisplatinum plus gemcitabine combination in advanced pancreatic cancer", J. Surg Oncol., vol. 95 (6), pp. 507-512 (2007) Abstract Only.

International Preliminary Report on Patentability for PCT/US2008/082223 filing date Nov. 3, 2008.

International Search Report for PCT/US2008/082223 dated Jan. 28, 2009.

International Search Report for PCT/US2011/32581 dated Jul. 5, 2011.

Johnson et al., "Can Cancer Tumors Be Starved to Death"? Retrieved Sep. 20, 2012 (online) <http://www.mhhe.com/biosci/genbio/t1w3/virtual_labs/lab6/labs/resources/original.pdf>.

Kragh et al., "Non-anti-coagulant heparin inhibits metastasis but not primary tumor growth", Oncology Reports, vol. 14, pp. 99-104 (2005).

Mao, et al. "Capillary electrophoresis for the analysis fo glycosaminioglycans and glycosaminoglycan-derived oligosaccharides" Biomedical Chromatography, vol. 16, pp. 77-94 (2002).

Mascellani et al., "Structure and Contribution to the heparin cofactor II-mediated inhibition of thrombin of naturally oversulphated sequences of dermatan sulphate" Biochem. J. vol. 296 pp. 639-648 (1993).

Naggi et al., "Modulation of the Heparanase-inhibiting Activity of Heparin through Selective Desulfation, Graded N-Acetylation, and Glycol Splitting", The Journal of Biological Chemistry, vol. 280, No. 13, pp. 12103-12113 (2005).

Peters et al., "Randomized comparison of a novel anticoagulant, vasoflux, and heparin as adjunctive therapy to streptokinase for acute myocardial infarction(vasoflux international trial for acute myocardial infarction lysis)", American Heart Journal., vol. 142 (2), pp. 237-243 (2001).

Pisano et al., "Undersulfated, low-molecular-weight glycol-split heparin as an antiangiogenic VEGFantagonist" Glycobiology, vol. 15, No. 2, pp. 1C-6C. (2005).

Ritchie et al., "A chemically modified heparin, inhibits myeloma growth and angiogenisis via disruption of the heparanase/syndecan-1 axis", Clin Can Res, pp. 1382-1393 (2011).

Sasisekharan et al., "Roles of Heparin-Sulphate Glycosaminoglycans in Cancer", Nature Reviews, vol. 2, pp. 521-528 (2002).

Spickler et al., "Clinical evaluation of the pharmacology, and safety of vasoflux[trademark symbol], a novel antithrombotic", Abstracts from the 70th scientific sessions, Nov. 9-12, 1997.

Weitz et al., "Vasoflux, a new anticoagulant with a novel mechanism of action", circ.ahajournals.org, pp. 682-689 (1999).

Written Opinion of the International Seaching Authority for PCT/US2011/32851 dated Jul. 5, 2011.

Written Opinion of the International Seraching Authority for PCT/US2008/082223.

Yamada et al., "Isolation of hte Porcine Heparin Testrasaccharides with Glucuronate 2-O-Sulfate" The Journal of Biological Cheminstry, vol. 270, No. 15, pp. 8696-8705 (1995).

Yang et al., "Targeting heparanase as a therapy for multiplemyeloma", Abstract # 257, Apr. 18, 2009.

(56) References Cited

OTHER PUBLICATIONS

Chinese Search Report from Chinese Application No. 201180019382.7 dated Jun. 7, 2014.
Bassas P et al., "Anticoagulation and Antiplatelet Therapy in Dermatology", ACTAS Dermosifiliograficas, vol. 100, No. 1, pp. 7-16 (2009).
Chu et al., "M-ONC 402, a novel low molecular weight heparin (LMWH) interacts with heparin-binding proteins and inhibits metastatic seeding of tumor cells in mice", Proceedings of the American Association for Cancer Research Annual Meeting, vol. 50, p. 1210 (2009).
De Lorenzo Ferruccio et al: "The role of anticoagulation in cancer patients: Facts and figures" Anti-Cancer in Agents Medicinal Chemistry, vol. 6, No. 6, pp. 579-587 (2006).
Derbyshire et al., "Anti-tumor and Anti-angiogenic effects in Mice of Heparin Conjugated to Angiostatic Steriods" Int. J. Cancer vol. 63 pp. 694-701 (1995).
Diaz-Montero et al., "Increased circulating myeloid-derived suppressor cells correlate with clinical cancer stage, mestastatic tumor burden, and doxorubicin-cyclophosphamide chemotherapy", Cancer Immunology Immunotherapy, vol. 58, No. 1 pp. 49-59 (2009).
Extended European Search Report from European Application No. 11769718.5 dated Jul. 12, 2013.
Ferro Vito et al: "PI-88 and novel heparan sulfate mimetics inhibit angiogenesis" Seminars in Thrombosis and Hemostasis, vol. 33, No. 5, pp. 557-562 (2007).
Gabrilovich Dmitry I et al: "Myeloid-derived suppressor cells as regulators of the immune system" Nature Reviews Immunology, vol. 9, No. 3, pp. 162-174 (2009).
Gerotziafas G T et al: "Clinical studies with anticoagulants to improve survival in cancer patients" Pathophysiology of Haemostasis and Thrombosis 2008 S. Karger AG CHE LNKD-DOI:10.1159/000175158, vol. 36, No. 3-4, pp. 204-211 (2008).
International Prelimnary Report of Patentability and Written Opinion from International Application Serial No. PCT/US2008/082224 dated Feb. 4, 2010.
International Search Report for PCT/US2011/32771 dated Nov. 23, 2011.
International Search Report including Written Opinion for PCT/US2011/040470 dated Oct. 16, 2012.
Kondo et al., "Favorable Prognosis of Renal Cell Carcinoma with Increased Expression of Chemokines Associated with a Th1-type Immune Response," Cancer Science, 2006, vol. 97, Iss. 8, pp. 780-786.
Matsumoto et al., "Granulocyte-colony Stimulating Factor-producing Esophageal Carcinoma: Serum Level as a Marker for Monitoring the Effects of Treatment," International Journal of Clinical Oncology, 2000, vol. 5, Iss. 5, pp. 328-333.
Mousa Shaker A: "Role of current and emerging antithrombotics in thrombosis and cancer" Drugs of Today, vol. 42, No. 5, pp. 331-350 (2006).
Ostrand-Rosenberg Suzanne et al: "Myeloid-Derived Suppressor Cells: Linking Inflammation and Cancer" Journal of Immunology, vol. 182, No. 8, pp. 4499-4506 (2009).
Riedel et al, "Serum Levels of Matrix Metalloproteinase-2 and -9 in Patients with Head and Neck Squamous Cell Carcinoma," Anticancer Research, 2000, vol. 20, pp. 3045-3050.
Wang et al., "Enoxaparin-induced alopecia in patients with cerebral venous thrombosis", Journal of Clinical Pharmacy and Therapeutics, vol. 31, No. 5, pp. 513-517 (2006).
Washimi et al., "Measurement of plasma matrix methalloproteinase-9 in diagnosing metastatic bone tumors and evaluating the therapeutic effect," 62nd Proceedings of the Japanese Cancer Association, 2003, p. 48, 3445-PA.
"Fragmin" by RxList: The Internet Drug Index. Retrieved on [Aug. 19, 2014] [online]. Retrieved from the internet at <http://www.rxlist.com/fragmin-drug.htm>.
Avci et al., "Synthetic Oligosaccharides as Heparin-Mimetics Displaying Anticoagulant Properties" Current Pharm. Design, 9:2323-2335 (2003).
Beccati et al., "Identification of a novel structure in heparin generated by potassium permanganate oxidation" Carbohydrate Polymers, 82:699-705 (2010).
Beyer, et al., "Composition of OSCS-contaminated heparin occurring in 2008 in batches on the German market" European Journal of Pharmaceutical Sciences, 40:297-304 (2010).
Gerotziafas et al., "Effect of the anti-factor Xa and anti-factor IIa activities of low-molecular-weight heparins upon the phases of thrombin generation" Journal of Thrombosis and Haemostasis, 5:955-962 (2007).
Halsall et al., "Oxidation of Carbohydrate by the Periodate Ion" Journal of Chemical Society, 172:1427-1432 (1947).
International Prelimnary Report of Patentability and Written Opinion from International Application Serial No. PCT/US2010/031480 dated Oct. 18, 2011.
International Prelimnary Report of Patentability and Written Opinion from International Application Serial No. PCT/US2011/032581 dated Oct. 16, 2012.
International Prelimnary Report of Patentability and Written Opinion from International Application Serial No. PCT/US2011/032771 dated Oct. 16, 2012.
International Search Report for PCT/US2008/082224 dated May 20, 2009.
International Search Report for PCT/US2010/031480 dated Sep. 27, 2010.
International Search Report for PCT/US2011/032581 dated Jul. 5, 2011.
International Search Report for PCT/US2014/039538 dated Oct. 1, 2014.
International Search Report for PCT/US2014/039542 dated Oct. 1, 2014.
Sakuma et al., "Particulate Phase of Cellulose Cigarrette Smoke" Agric. Biol. Chem., 44(3):555-561 (1980).
Addison, et al., "The CXC Chemokine, Monokine Induced by Interferon-gamma, Inhibits Non-Small Cell Lung Carcinoma Tumor Growth and Metastasis" Human Gene Therapy, 11:247-261 (2000).
Hilbe, et al., "CD133 positive endothelial progenitor cells contribute to the tumour vasculature in non-small cell lung cancer" J Clin Pathol, 57:965-969 (2004).
Kragh, et al., "Non-anti-coagulant heparins: A promising approach for prevention of tumor metastasis (Review)" International Journal of Oncology, 27:1159-1167 (2005).
Lolkema, et al., "Abstract LB-43:M402, a novel heparin sulphate mimetic, synergizes with gemcitabine to improve survival and reduce metastasis and epithelial-to-mesenchymal transition (EMT) in a genetically engineered mouse model for pancreatic cancer" Cancer Research, 70(8 Suppl): Abstract LB-43 (2010).
Natori, et al., "G-CSF stimulates angiogenesis and promotes tumor growth: potential contribution of bone marrow-derived endothelial progenitor cells" Biochemical and Biophysical Research Communications, 297:1058-1061 (2002).
Yamashita, et al., "Immunoreactive Hepatocyte Growth Factor is a Strong and Independent Predictor of Recurrence and Survival in Human Breast Cancer" Cancer Research, 54:1630-1633 (1994).
Yao, et al., "Multiple signaling pathways involved in activation of matrix metalloproteinase-9 (MMP-9) by hereguling-beta1 in human breast cancer cells" Oncogene, 20:8066-8074 (2001).
Zea, et al., "Arginase-Producing Myeloid Suppressor Cells in Renal Cell Carcinoma Patients: A Mechanism of Tumor Evasion" Cancer Res., 65(8):3044-3048 (2005).
Zhou, et al., "Abstract #281: M-ONC 402-a non anticoagulant low molecular weight heparin inhibits tumor metastasis" Cancer Research, 69:Abstract 281 (2009).
Linhardt, R.J., Gunay, N.S. (1999) Production and Chemical Processing of Low Molecular Weight Heparins. Seminars in Thrombosis and Hemostasis, vol. 25, suppl. 3, p. 5-16.
Kennett, E.C., Davies, M.J. (2009) Glycosaminoglycans are fragmented by hydroxyl, carbonate, and nitrogen dioxide radicals in a site selective manner: implications for peroxynitrite-mediated damage at sites of inflammation. Free Radical Biology & Medicine, vol. 47, p. 389-400.

(56) References Cited

OTHER PUBLICATIONS

Koliopanos, A., Friess, H., Kleef, J., Shi, X., Liao, Q., Peeker, I., Vlodaysky, I., Zimmermann, A., Buchler, M.W. (2001) Heparanase Expression in Primary and Metastatic Pancreatic Cancer. Cancer Research, vol. 61, p. 4655-4659.

Ansel, H.C., Allen, Jr., L.V., Popovich, N.G. (1999) Pharmaceutical Dosage Forms and Drug Delivery Systems, Published by Lippincott Williams & Wilkins, p. 48-53 and 120-128.

Safran, H., Dipetrillo, T., Iannitti, D., Quirk, D., Akerman, P., Gruff, D., Cioffi, W., Shah, S., Ramdin, N., Rich, T. (2002) International Journal of Radiation Oncology Biology Physics, vol. 54, No. 1, p. 137-141.

Gradishar, W.J. (2006) Albumin-bound paclitaxel: a next-generation taxane. Expert Opinion in Pharmacotherapy, vol. 7, No. 8, p. 1041-1053.

* cited by examiner

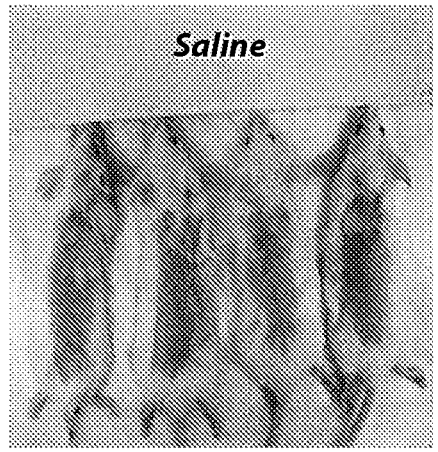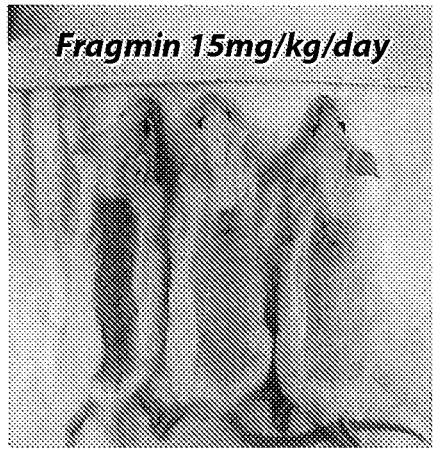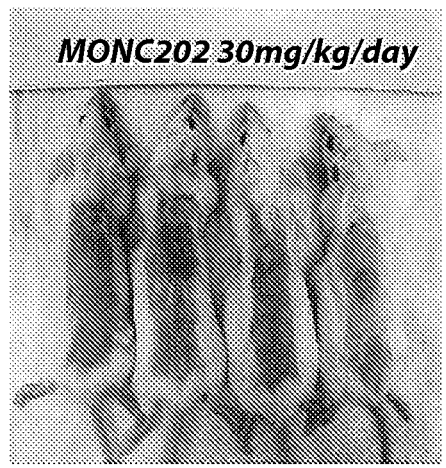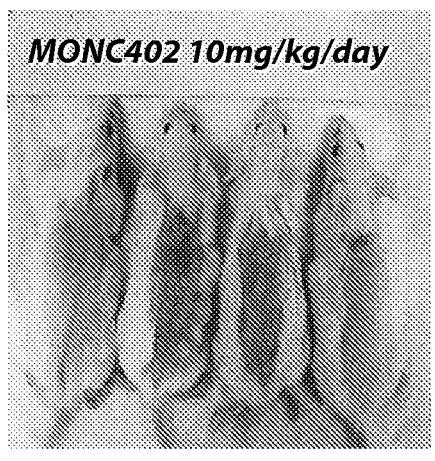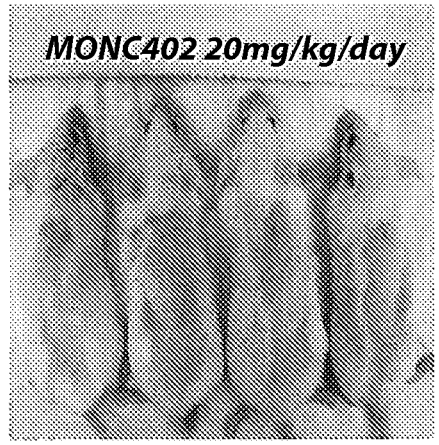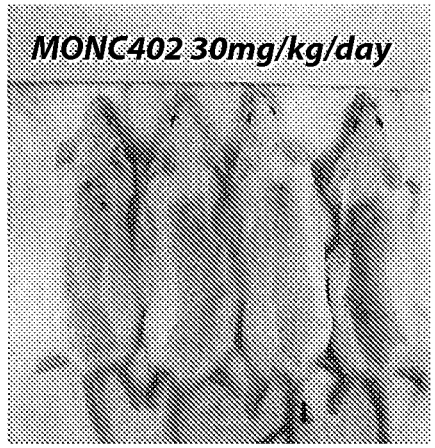

METHODS AND COMPOSITIONS FOR PROMOTING HAIR GROWTH

BACKGROUND OF THE INVENTION

Heparin-related compounds are widely used as anticoagulants and anti-thrombotic agents. They have also been reported to inhibit hair growth. See Wang and Po (2006) *Enoxaparin-induced alopecia in patients with cerebral venous thrombosis. J Clin Pharm Ther* 31(5):513-7; Tsele et al. (2003) *Diffuse alopecia in a hemodialysis patient caused by a low-molecular-weight heparin, tinzaparin. Am J Kidney Dis* 41:E15; Paus (1991) *Hair growth inhibition by heparin in mice: a model system for studying the modulation of epithelial cell growth by glycosaminoglycans? Br J Dermatol* 124:415-22.

SUMMARY OF THE INVENTION

The invention is based, at least in part, on the discovery that low molecular weight heparin (e.g., a LMWH described herein, e.g., a LMWH having reduced anticoagulant activity) can promote hair growth. Accordingly, the invention features, inter alia, methods to increase hair growth, and related pharmaceutical, veterinary and/or cosmetic preparations.

As used herein "hair" means scalp, head, facial and/or body hair, including but not limited to hair on the scalp, eyelashes, brows, mustache, and beard.

As used herein "inducing hair growth" means the earlier induction (compared to a control) of growth of a new hair cycle, and/or prolonging the active growth phase of the hair cycle, and/or increasing the growth rate of the hair, and/or increasing the width of hair shaft, including, but not limited to, the induction of the growth of hair and making it more visible to the eye.

As used herein, to administer two or more agents "in combination" means that the individual agents are administered concurrently or within a time interval such that the physiological effects of the agents on the subject overlap. The two or more agents may or may not be administered in the same formulation or preparation.

BRIEF DESCRIPTION OF THE FIGURES

FIG. 1 shows photographs of shaved mice treated by osmotic pump with saline, Fragmin, MONC402 or MONC202, after 16 days of treatment.

DETAILED DESCRIPTION

Hair Loss

Alopecia is the loss or thinning of hair on the head or body in humans, or loss of wool or feathers in animals. Heredity, hormonal effects, certain diseases, and certain drugs and treatments can contribute to alopecia. Alopecia becomes more common as age increases, but hair loss may start at younger ages.

Chemotherapy-induced alopecia is a problem in clinical oncology. Certain chemotherapeutic agents, for example, antimetabolites (methotrexate, 5-fluoouracil, cytarabine), alkylating agents (cyclophosphamide, mechlorethamine, dacarbazine, ifosfamide), antineoplatic antibiotics (bleomycin, actinomycin D, daunomycin, doxorubicin, mitoxantrone), the vinca alkaloids (vincistine, vinblastine) and taxanes (Taxol, Taxotere), produce an anagen effluvium to induce alopecia, presumably by killing the active proliferating cells of the hair matrix. Scalp hair is particularly sensitive.

Low Molecular Weight Heparins

A LMWH described herein can be used in methods to induce hair growth.

In one embodiment, the LMWH is a LMWH produced by nitrous acid depolymerization, e.g., dalteparin or M402.

In some embodiments, a LMWH can have the following features: (a) reduced anticoagulant activity, e.g., anti-factor Xa activity (anti-Xa activity and anti-factor IIa activity (anti-IIa activity) each less than 50 IU/mg, 20 IU/mg, 10 IU/mg, 5 IU/mg or less (e.g., between about 0.5-10 IU/mg, between 0.5-5 IU/mg, between 1-10 IU/mg, between 1-5 IU/mg; (b) glycol split uronic acid residues (e.g., less than 50%, 40%, 30%, 20%, of the uronic acid residues are glycol split uronic acid residues); (c) weight average molecular weight between 3,500 and 8,000 Da, e.g., between 4,000 and 8,000 Da.

In some embodiments, the LMWH may additionally have one or more (e.g., 2, 3, 4, 5, 6, 7, 8, or 9, 10, 11) of the following properties:

(d) greater than 40% $U_{2S}H_{NS,6S}$ disaccharide residues;

(e) degree of desulfation less than 40%;

(f) one or more polysaccharide chains have a 4,5-unsaturation of a non-reducing end uronic acid residue;

(g) one or more polysaccharide chains have a 2,5-anhydromannitol residue at the reducing end;

(h) no more than 3 glycol split uronic acid residues ($U_G$) per polysaccharide chain;

(i) 10-50% (e.g., 10-40%, 10-30%, 15-30% or 15-25%) of the oligosaccharides of the LMWH have a molecular weight <3000 Da;

(j) 40-65% (e.g., 40-60%, 45-65%, 50-65%, or 55-65%) of the oligosaccharides of the LMWH have a molecular weight between 3000-8000 Da;

(k) 5-30% (e.g., 10-30%, 15-30%, 10-25%, or 15-25%) of the oligosaccharides of the LMWH have a molecular weight >8000 Da;

(l) polydispersity of about 1.2 to 1.7 (e.g., about 1.3 to 1.7, 1.4 to 1.6, or 1.3 to 1.6);

(m) consists essentially of polysaccharides that include Formula I: $[U_w\text{—}H_{x,y,z}]_m\sim[U_G\text{—}H_{x,y,z}]_n$ wherein U indicates a uronic acid residue and H indicates a hexosamine residue; wherein m and n are integers such that m=4-16, and n=1-4; w=–2OS or –2OH; x=—NS or —N-acetylcysteine (NAc); y=–3OS or –3OH; z=–6OS or –6OH; and $U_G=$

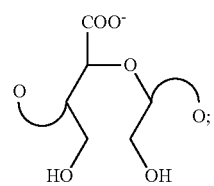

wherein the symbol ~ indicates that the units marked m and n are distributed along the polysaccharide chain and are not necessarily in sequence, wherein w, x, y, and z are each the same or different on each unit marked m, and wherein x, y, and z are each the same or different on each unit marked n;

(n) consists essentially of polysaccharides that include Formula II: $[U_w\text{—}H_{x,y,z}]_m\text{—}[U_G\text{—}H_{x,y,z}]_n\text{—}[U_w\text{—}H_{x,y,z}]_o\text{—}[U_G\text{—}H_{x,y,z}]_p\text{—}[U_w\text{—}H_{x,y,z}]_q$ wherein U indicates a uronic acid residue and H indicates a hexosamine residue; wherein m-r are integers such that: m=0-10; n=0-3; o=0-10; p=0-3; q=0-10; w=−2OS or −2OH; x=—NS or —NAc; y=−3OS or −3OH; z=−6OS or −6OH; and $U_G=$

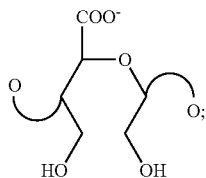

wherein w, x, y, and z are each the same or different on each unit marked m, n, o, p, or q.

In the above, each of w, x, y, and z can be the same or different for each occurrence of $[U_w—H_{x,y,z}]$, and each of x, y, and z can be the same or different for each occurrence of $[U_G—H_{x,y,z}]$. Each occurrence of U can independently be an iduronic acid (I) or a glucuronic acid (G). In some embodiments, the sum of n+p is less than or equal to 4 (e.g., less than or equal to 3, 2, 1, or 0). In some embodiments, the sum of n and p is 4, 3, 2 or 1. In some embodiments, the sum of m, o and q is between 4 and 18, e.g., 4-8, 4-9, 4-10, 4-11, 4-12, 4-13, 4-14, 4-15, 4-16 or 4-17.

In one embodiment, at least one of the polysaccharide chains in the LMWH preparation has one of the following structures at the non-reducing end:

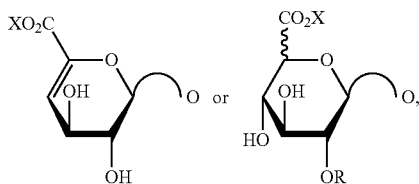

wherein X is H or Me and R is H or $SO_3$. For example, about 10%, 20%, 30%, 40%, 50%, 60%, 70%, 80%, 90%, or substantially all of the non-reducing ends of the preparation or pharmaceutical composition have the structure.

In one embodiment, at least one of the polysaccharide chains in the preparation or pharmaceutical composition includes a 2,5-anhydromannitol residue at the reducing end. For example, about 10%, 20%, 30%, 40%, 50%, 60%, 70%, 80%, 90%, or substantially all of the polysaccharide chains in the preparation or pharmaceutical composition include a 2,5-anhydromannitol residue at the reducing end.

Anti-IIa activity is calculated in International Units of anti-IIa activity per milligram using statistical methods for parallel line assays. The anti-IIa activity levels described herein are measured using the following principle.

Polysaccharide (PS)+ATIII (antithrombin)→ [PS•ATIII]

IIa

PS•ATIII→[PS•ATIII•IIa (factor IIa)]+IIa (Excess)

IIa (Excess)+Substrate→Peptide+paranitroanaline (pNA) (measured spectrophotometrically)

Anti-factor IIa activity is determined by the sample potentiating effect on antithrombin (ATIII) in the inhibition of thrombin. Thrombin excess can be indirectly spectrophotometrically measured. The anti-factor IIa activity can be measured, e.g., on a Diagnostica Stago analyzer or on an ACL Futura3 Coagulation system, with reagents from Chromogenix (S-2238 substrate, Thrombin (53 nkat/vial), and Antithrombin), or on any equivalent system. Analyzer response is calibrated using the 2nd International Standard for Low Molecular Weight Heparin.

Anti-Xa activity of a preparation is calculated in International Units of anti-factor Xa activity per milligram using statistical methods for parallel line assays. The anti-factor Xa activity of preparations described herein is measured using the following principle:

PS+ATIII→[PS•ATIII]

Factor Xa (FXa)

PS•ATIII→[PS•ATIII•FXa]+FXa(Excess)

FXa (Excess)+Substrate→Peptide+pNA (measured spectrophotometrically)

The anti-factor Xa activity is determined by the sample potentiating effect on antithrombin (ATIII) in the inhibition of activated Factor Xa (FXa). Factor Xa excess can be indirectly spectrophotometrically measured. Anti-factor Xa activity can be measured, e.g., on a Diagnostica Stago analyzer with the Stachrom® Heparin Test kit, on an ACL Futura3 Coagulation system with the Coatest® Heparin Kit from Chromogenix, or on any equivalent system. Analyzer response can be calibrated using the NIBSC International Standard for Low Molecular Weight Heparin.

Molecular Weight and Chain Length:

When weight average molecular weight of a preparation is determined, a weight average molecular weight of about 3500 to 8000 Da, about 3500 to 6300 Da, preferably about 4000 to 6000 Da, about 4200 to 5900, or about 4300 to 5800 Da, indicates that a significant number of chains in the polysaccharide preparation are of sufficient chain length. "Weight average molecular weight" as used herein refers to the weight average in daltons of chains of uronic acid/hexosamine disaccharide repeats. The presence of non-uronic acid and/or non-hexosamine building blocks are not included in determining the weight average molecular weight. Thus, the molecular weight of non-uronic acid and non-hexosamine building blocks within a chain or chains in the preparation should not be included in determining the weight average molecular weight. The weight average molecular weight $(M_w)$ is calculated from the following equation: $M_w=\Sigma(c_i m_i)/\Sigma c_i$. The variable $c_i$ is the concentration of the polymer in slice i and $m_i$ is the molecular weight of the polymer in slice i. The summations are taken over a chromatographic peak, which contains many slices of data. A slice of data can be pictured as a vertical line on a plot of chromatographic peak versus time. The elution peak can therefore be divided into many slices. The weight average molecular weight calculation is average dependant on the summation of all slices of the concentration and molecular weight. The weight average molar weight can be measured, e.g., using the Wyatt Astra software or any appropriate software. The weight average molecular weights described herein are determined by high liquid chromatography with two columns in series, for example a TSK G3000 SWXL and a G2000 SWXL, coupled with a multi angle light scattering (MALS) detector and a refractometric detector in series. The eluent used is a 0.2 M sodium sulfate, pH 5.0, and a flow rate of 0.5 mL/min.

A determination of whether a polysaccharide preparation includes chains of sufficient chain length can be made, for example, by determining the average chain length of the chains in the preparation and/or by determining the weight average molecular weight of chains within the preparation. When average chain length is determined, an average chain length of about 5 to 22, e.g., about 7 to 18, typically about 7 to 14 or 8 to 13 disaccharide repeats, indicates that a significant number of chains in the preparation are of sufficient chain length.

"Average chain length" refers to the average chain length of uronic acid/hexosamine disaccharide repeats that occur within a chain. The presence of non-uronic acid and/or non-hexosamine building blocks (e.g., attached PEG moieties) are not included in determining the average chain length. Average chain length is determined by dividing the number average molecular weight (Mn) by the number average molecular weight for a disaccharide (500 Da).

Glycol Split Uronic Acids:

A polysaccharide preparation described herein can include an opening of the glycoside ring, conventionally called reduction-oxidation (RO) derivatives. In these preparations, one or more glycoside rings having vicinyl dials that are opened, e.g., at the bond between C2 and C3, by means of an oxidation action, followed by a reduction. The compounds referred to herein will also be called "Glycol Split" derivatives. In a further embodiment of the invention described herein, the glycol split residues lend themselves to the subsequent functionalization. Therefore, the compounds may also bear equal or different groups, in place of the primary hydroxy groups deriving from glycol split, for example, aldehyde groups, methoxy groups, or oligosaccharide or peptide groups, ranging from a single saccharide or amino acid to more than one unit of length, e.g., 2 or 3 units.

In some embodiments, fewer than 50% of the uronic acid residues are glycol split uronic acid residues (e.g., less than 40%, 30%, 25%, or 20% of the uronic acid residues are glycol split uronic acid residues).

Reducing End Structures:

In some instances, at least about 50% of the chains in a polysaccharide preparation described herein have a modified reducing end structure such as a 2,5-anhydromannose residue or a 2,5-anhydromannose that has been reduced to form an alcohol. In some embodiments, at least about 55%, 60%, 65%, 70%, 75%, 80%, 85%, 90%, or 95% of the oligosaccharide chains in the preparation have a modified reducing end structure, such that the reducing end includes a 2,5-anhydromannose residue or a 2,5-anhydromannose that has been reduced to form an alcohol.

Polydispersity:

The polydispersity of polysaccharide preparations provided herein is about 2 or less, e.g., 1.7 or less, e.g., about 1.7 or 1.6 to 1.2, about 1.4-1.5, and numbers in between. The term "polydisperse" or "polydispersity" refers to the weight average molecular weight of a composition (Mw) divided by the number average molecular weight (Mn). The number average molecular weight (Mn) is calculated from the following equation: Mn=$\Sigma c_i/(\Sigma c_i/m_i)$. The variable $c_i$ is the concentration of the polysaccharide in slice i and $M_i$ is the molecular weight of the polysaccharide in slice i. The summations are taken over a chromatographic peak, which contains many slices of data. A slice of data can be pictured as a vertical line on a plot of chromatographic peak versus time. The elution peak can therefore be divided into many slices. The number average molecular weight is a calculation dependent on the molecular weight and concentration at each slice of data. Methods of determining weight average molecular weight are described above, and were used to determine polydispersity as well.

Methods of Making LMWH Described Herein

One method includes providing a precursor LMWH preparation such as unfractionated heparin (UFH) and processing the precursor heparin preparation (e.g., by enzymatic or chemical depolymerization, e.g., by nitrous acid depolymerization) to obtain a LMWH preparation having a weight average molecular weight of about 3000 to 7000 Da or an average chain length of about 7 to 18 disaccharides.

The precursor heparin preparation can be processed by a method comprising depolymerization (e.g., by nitrous acid treatment, hydrolysis, or enzymatic depolymerization) optionally followed by a glycol split reaction. Nitrous acid depolymerization can be accomplished, e.g., by treating the precursor heparin preparation (e.g., UFH) with nitrous acid (e.g., about 0.02 to 0.04 M nitrous acid) at a pH of about 2 to 4 for a specified period of time (e.g., about 1 to 5 hours) at a temperature of about 10 to 30° C. The glycol split reaction involves periodate oxidation using periodate (e.g., about 0.05 M to 0.2 M sodium periodate) for about 10 to 20 hours at a temperature of about 0 to 10° C. In some embodiments, residual impurities such as salts or diethylene glycol (DEG) can be subsequently removed by a chromatographic method, e.g. gel filtration chromatography. Optionally, the oxidized preparation is then reduced by treatment with a reducing agent (e.g., about 0.5 to 2.0% (w/v) sodium borohydride) for about 0.5 to 3 hours at a pH of about 6.0 to 7.0 and a temperature of about 0 to 10° C.

A precursor heparin preparation can be processed using enzymatic digestion, chemical digestion or combinations thereof. Examples of chemical digestion include oxidative depolymerization, e.g., with $H_2O_2$ or $Cu^+$ and $H_2O_2$, deaminative cleavage, e.g., with isoamyl nitrite or nitrous acid, β-eliminative cleavage, e.g., with benzyl ester, and/or by alkaline treatment. Enzymatic digestion can include the use of one or more heparin degrading enzymes. For example, the heparin degrading enzyme(s) can be, e.g., one or more heparinase, heparin lyase, heparin sulfate glycoaminoglycan (HSGAG) lyase, a lyase described as a glycoaminoglycan (GAG) lyase that can also degrade heparin. Preferably, the enzyme cleaves at one or more glycosidic linkages of unsulfated uronic acids.

Formulation and Administration

The LMWH described herein can be formulated as pharmaceutical or cosmetic compositions for promoting hair growth on areas of the body showing hair thinning or hair loss (alopecia). Such compositions typically include appropriate pharmaceutically or cosmetically acceptable carriers (such as buffering agents, adjuvants, lubricants, solvents, emollients) and, optionally, other pharmaceutical or cosmetic agents, using well known formulation protocols. Administration of the compositions can be accomplished using an appropriate vehicle, e.g., injectable solutions, oral dosage forms, topical dosage forms. Administration can be, e.g., intravenously, subcutaneously, orally or topically. The precise amount of the LMWH used in the composition will be determined based on the nature of the formulation and dosing regimen. A dose may be 25 mg-1 g/day but the dosage form will depend on the route of administration. For example, for a parenteral dose, 0.5-5 mg/kg (e.g., 1-2 mg/kg) may be appropriate, whereas if administered topically, the dosage form may be about 0.1-10 mg/mL (e.g., about 1 mg/mL). Administration will typically be chronic, i.e., multiple doses over a period of time, e.g., once or twice a day for at least 4, 7, 10, 15, 21, 30, 45, 60, 90 days or more; or e.g., every other day for at least 4, 7, 10, 15, 21, 30, 45, 60, 90 days or more. The LMWH compositions described herein may be utilized to induce hair growth to the area of the body on which hair growth is desired or needed.

For parenteral administration (e.g., intravenous or subcutaneous administration) the LMWH can be incorporated into a solution or suspension, which may also contain one or more adjuvants, e.g., sterile diluents such as water for injection, saline, antibacterial agents, antioxidants, chelating agents, buffers and agents for adjusting the tonicity. The parenteral preparation can be provided in vials, ampoules, syringes or as infusions. The making of parenteral preparations of heparin and heparin-based agents is routine in the art.

Methods of making oral formulations of heparin-based compounds are known in the art. For example, Baughman et al. (*Oral Delivery of Anticoagulant Doses of Heparin: A randomized, double blind, controlled study in humans* (1998) *Circulation* 98:1610-1615) describe heparin administered orally in combination with the delivery agent sodium N-[8(-2-hydroxybenzoyl)amino]caprylate (SNAC). Kim et al. (*A newly developed oral heparin derivative for deep vein thrombosis: Non-human primate study* (2007) *J Controlled Release* 123:155-163) describe an active orally active heparin, Db-LHD, in a solid dosage form. US 2010-0081708 describes orally available LMWHs. Accordingly, a LMWH described herein can be provided as an oral formulation using routine methods.

For oral administration, LMWH described herein may be provided in the form of tablets, capsules, aqueous solutions, gelatins or suspensions. In such, the active ingredient may be mixed with pharmaceutically or cosmetically acceptable excipients such as inert diluents, binding agents, lubricating agents, sweetening agents, pigments, flavoring agents, coloring agents and preservatives. Inert diluents include sodium and calcium carbonate, sodium and calcium phosphate and lactose. Lubricating agents include oils, magnesium stearate, stearic acid or talc. Tablets or capsules may be coated with a material to delay absorption in the gastrointestinal tract, e.g., lyceryl monostearate or glyceryl distearate. Slow release formulations, such as liposomes, microspheres, pegylated LMWH are also included. Such oral formulations comprise usually at least about 1%, 2%, 3%, 4%, 5%, 10%, 15%, 20%, 30%, 40%, 50% or more of the LMWH. A typical dosage regimen for oral administration may be 25-100 mg/day, but may be up to 1 g or more. In one embodiment, the LMWH compositions described herein are administered as a dietary supplement by way of a capsule, tablet, or aqueous solution, e.g., taken once a day, twice a day, once a week, biweekly, semiweekly, or monthly.

The making of topical formulations of heparin-based compounds is also routine in the art. For example, topical heparin gel (Lioton® or Menaven®) is widely used in Europe in the prevention and treatment of local symptoms associated with peripheral vascular disorders. U.S. Pat. No. 5,888,984 and U.S. Pat. No. 5,668,119 describe topical preparations of heparin and other glycosaminoglycans. Vecchio and Frisinghelli (Topically applied heparins for the treatment of vascular disorders: a comprehensive review. Clin Drug Investig (2008) 28:603-14) and Cesarone et al (*Topical Heparin: New Observations* (2007) Angiology 58:16 S-20S) describe heparin gels and other heparin-based topical products. Song and Kim (*Topical delivery of low-molecular-weight heparin with surface-charged flexible liposomes* (2006) *Biomaterials* 27:271-280) describe topical preparations of LMWH. Accordingly, a LMWH described herein can be provided as a topical formulation using routine methods, i.e., a preparation may be formulated in accordance with conventional pharmaceutical or cosmetic practice with pharmaceutical or cosmetic excipients conventionally used for topical applications. The nature of the vehicle employed in the preparation of any particular composition will depend on the method intended for administration of that composition.

A topical preparation described herein may be formulated in a variety of product forms, such as a lotion, cream, serum, spray, aerosol, emulsion, cake, ointment, essence, gel, mousse, paste, patch, pencil, towelette, mask, stick, foam, elixir, concentrate, and the like. The preparations can include one or more of: a solvent, an emulsifier, an emollient, a slip aid (e.g., a silicone), a humectant, a fragrance, a pigment or coloring, a preservative, a surfactant, a thickener, a sequestering agent, a wax, an oil, a gelling agent, a pearlising agent, a pH adjusting agent. Topical compositions described herein may also be in the form of shampoo, hair conditioning products, leave-on hair mask, hair mousse, hair gel, hairspray, optionally in combination with a dye and/or other hair care product for cleaning, styling, treating, conditioning or coloring the hair simultaneous with topical application of the LMWH described herein. Acceptable vehicles include water (e.g., deionized water); oils such as vegetable oils or mineral oils; esters such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and biphenyl alcohol; isoparaffins such as isooctane, isododecane and is hexadecane; silicone oils such as cyclomethicone, dimethicone, dimethicone cross-polymer, polysiloxanes and their derivatives, preferably organomodified derivatives; polyethylene glycols; hydrocarbon oils such as mineral oil, petrolatum, isoeicosane and polyisobutene; polyols such as propylene glycol, glycerin, butylene glycol, pentylene glycol and hexylene glycol; waxes such as beeswax and botanical waxes; or any combinations or mixtures of the foregoing.

Topical LMWH preparations described herein may comprise between 0.01-50% w/w of the LMWH. For example, a topical preparation may comprise between 0.5-30% w/w LMWH, between 1-20% w/w LMWH, between 1-10% w/w LMWH. Topical formulations may then be applied to the desired areas of the body (e.g., scalp or eyebrow area), e.g., from 1 to 4 times daily. Alternatively, these formulations can be applied to the desired areas less frequently, i.e., from 1 to 5 times a week. In one embodiment, the LMWH preparation is applied topically to the desired area of the body at least once per day for at least three weeks, four weeks, twelve weeks or longer, e.g., indefinitely.

Combinations

The LMWH described herein may also be utilized in combination with other active compounds, e.g., other agents to promote hair growth, e.g., finasteride (Propecia®), minoxidil (Rogaine®); vitamins (such as vitamin A, vitamin B3, vitamin B5, and vitamin B12, vitamin C, vitamin K, vitamin E and mixtures thereof); hydroxy acids (such as glycolic acid, lactic acid, malic acid, salicylic acid, citric acid, and tartaric acid); chemical and physical sunscreens (e.g., Mexoryl®, avobenzene, octinoxate, octisalate, oxybenzone, titanium dioxide, zinc oxide); antioxidants (e.g., sulfhydryl compounds and their derivatives such as sodium metabisulfite and N-acetyl-cysteine, lipoic acid and dihydrolipoic acid, resveratrol, lactoferrin, and ascorbic acid and ascorbic acid derivatives, butylated hydroxytoluene); retinoids such as retinol and retinyl palmitate; tocopherols and their esters; progesterones and naturally-derived ingredients with progesterone-like activity; darkening agents (e.g., melanin or synthetic melanin derivatives, or melanin-like molecules, vanillin polymers, natural extracts or pigments such as brown pigments from plants from the Hedychium genus or Bearberry genus or yellow, orange and red pigments from plants containing carotenoids or canthaxanthins; anti-dandruff agents such as coal tar or ketoconazole; peptides such as palmitoyl pentapapeptide (Matrixyl®). Such additional agents may be provided separately from a LMWH preparation described herein or may be present in the same preparation, e.g., in an amount from about 0.001% to about 10% by weight, in particular in an amount from about 0.01% to about 5% by weight.

EXAMPLES

Example 1: Preparation of a LMWH

Glycol Split low molecular weight heparin alcohol (GS-LMWH-CH2-OH) is generated from unfractionated heparin (UFH) by controlled nitrous acid depolymerization followed by oxidative glycol-splitting and subsequent reduction to an alcohol. In the first step, UFH is depolymerized to obtain depolymerized heparin (DPH-CHO) having an anhydromannose moiety at the reducing end of the polysaccharide. This is followed by Step II oxidative cleavage of the 2,3-dials present in the depolymerized heparin with sodium periodate to generate ring opened glycol split residues along the heparin chain (GS-DPH-CHO). The Step III involves a reduction step, wherein the aldehydic moieties are converted to alcohols using sodium borohydride to generate Glycol Split low molecular weight heparin alcohol. The following paragraphs describe the steps in the preparation in more detail.

Depolymerization:

UFH is dissolved in 10-fold volume of de-ionized water equilibrated at room temperature. The pH of this solution is adjusted to pH 3.1, and sodium nitrite (0.03 M) is added. This reaction solution is allowed to stir for several hours following which the pH is neutralized prior to addition of sodium chloride (same amount as starting UFH material). After complete dissolution of salt, at least 2 volumes of methanol are added with constant stirring. The precipitate obtained is aged at about room temperature for about 1 hour. This precipitate is then filtered and dried to obtain DPH in 80-85% typical yield.

Periodate Oxidation:

The aldehyde obtained in Step I is dissolved in about 10 volumes of water equilibrated at 5° C. To this solution is added an equal volume of cooled NaIO4 solution (0.1M) and the reaction mixture is stirred for 16 hours. On completion, the reaction is quenched by the addition of an alcohol, following which the temperature is raised back to room temperature. Sodium chloride (double the amount as starting aldehyde material) is then added to this solution, followed by addition of at least 3 volumes methanol to precipitate the heparin. The precipitate is allowed to age at about room temperature for 2 hours before filtration and drying to yield a glycol-split polysaccharide (typically about 95-98% yield).

Reduction:

The glycol split polysaccharide obtained in Step II is dissolved in 10 volumes of water maintained at 5° C. To this solution is added sodium borohydride (one tenth the starting amount of GS polysaccharide) and the reaction mixture is subsequently stirred for 1 hour. The reaction mixture is then brought to room temperature, followed by the addition of sodium chloride (same amount as the starting amount of GS polysaccharide). Following salt dissolution, 2 volumes of methanol is added to this solution accompanied with constant stirring. The precipitate thus obtained is aged at about room temperature before filtration and drying to yield the desired product. A MONC402 LMWH-sodium preparation with the following characteristics is thus obtained in approximately 55-60% yield:

Mw: 5000-7800 Daltons
Mw Distribution: (i) <3000 Daltons: 15-25%
(ii) 3000-8000 Daltons: 55-65%
(iii) >8000 Daltons: 15-25%
Anti-Xa Activity: 1-20 IU/mg
Anti-IIa Activity: 1-20 IU/mg Example 2: Effect of MONC402 on Hair Growth In many experimental animal models of cancer, animals are routinely shaved in certain areas, such as the abdomen or back, to facilitate the inoculation or implantation of cancer cells, injections, implantation of pumps, etc. In the course of analyzing the effects of MONC402 in such mouse tumor models, we unexpectedly observed that tumor-bearing mice treated with MONC402 had consistently faster regrowth of hair in the shaved areas than mice treated with saline as a control.

To further study this observation, we conducted an experiment to assess the effect of MONC402 on hair growth in normal mice. The backs of eight week old female BALB/c mice were shaved. Osmotic pumps containing saline, fragmin, MONC402 or MONC202 (N-desulphated LMWH derived from nitrous acid depolymerization of UFH) were implanted in four shaved mice per treatment group. Staples used to close the implantation wound were removed seven days later. Mice were sacrificed 16 days after osmotic pump implantation. (One mouse receiving fragmin died before the end of the experiment). The mice were photographed (see FIG. 1) and scores for hair growth over the shaved area were determined for each mouse prior to sacrifice (Table 1).

TABLE 1

| | Number of animals scored with each treatment | | | | | |
|---|---|---|---|---|---|---|
| score | Saline | MONC202 30 mg/kg/day | Fragmin 15 mg/kg/day | MONC402 10 mg/kg/day | MONC402 20 mg/kg/day | MONC402 30 mg/kg/day |
| 0: no visible regrowth | 4/4 | 2/4 | 1/3 | 2/4 | — | — |
| 1: Very thin or patchy regrowth | — | 1/4 | — | — | — | — |
| 2: thin regrowth | — | 1/4 | — | 1/4 | 1/4 | 1/4 |
| 3: Moderate regrowth | — | — | 2/3 | 1/4 | 3/4 | 3/4 |
| 4: full regrowth (indistinguishable from unshaved) | — | — | — | — | — | — |

As shown in Table 1, none of the control, saline-treated animals exhibited visible hair regrowth during the test period. 2 of 4 mice treated with MONC202 control (nitrous acid depolymerized, N-desulfated LMWH) showed only slight (very thin or thin) hair growth by 16 days. In contrast, MONC402-treated mice exhibited greater levels of hair regrowth. Mice treated with 20 and 30 mg/kg/day of MONC402 showed greater effects (3 of 4 mice having moderate hair growth) than 10 mg/kg/day, indicative of a dose dependent response.

Example 3: Effect of MONC402 on Hair Growth in Combination with Chemotherapy

This example shows the effect of MONC402 on hair growth when MONC402 is administered in combination with a chemotherapeutic agent.

The backs of eight week old female BALB/c mice were shaved. Osmotic pumps containing either saline or MONC402 were implanted into 64 mice (32 saline, 32 MONC402). Mice were further divided into groups receiving either saline or Docetaxel (10 mg/kg) once weekly ip starting 13 days after pump implant. Additionally, there was one group of naïve mice (n=4) as well as one group of mice receiving chemotherapy alone (Docetaxel, 10 mg/kg, once weekly ip starting 6 days after pump implant, n=16) which were not subject to shaving or pump implant. Staples used to close the implantation wound were removed 7 days later. Twenty seven days after pump implant, mice were scored for hair growth over the shaved area.

As shown in Table 2, mice treated with MONC402 alone or in combination with Docetaxel exhibited fuller hair regrowth than controls at 27 days.

TABLE 2

| | | | Number of animals scored with each treatment | | | |
|---|---|---|---|---|---|---|
| Score | Naive | Saline + Saline | Saline + MONC402 (40 mg/kg/day) | Docetaxel (10 mg/kg weekly ip) + Saline | Docetaxel + MONC402 | Docetaxel (No shaving or pump implant) |
| 1: no growth | | | | | | |
| 1.5 | | 1/16 | | 1/16 | | |
| 2: light growth | | 9/16 | | 7/16 | | |
| 2.5 | | 2/16 | | 2/16 | | |
| 3: patchy/heavy growth | | 4/16 | | 6/16 | 1/16 | |
| 3.5 | | | 16/16 | | 14/16 | |
| 4: full growth (indistinguishable from unshaved) | 4/4 | | | | 1/16 | 16/16 |

Example 4: Topical Preparation of LMWH

This example describes preparation of a LMWH gel cream, essentially as described for heparin-sodium gel cream by *Handbook of Pharmaceutical Manufacturing Formulations: Semisolid Products*. Niazi, Ed. 2d Edition, 2009.

Per 100 g scale manufacturing, the following is provided: 0.2 g LMWH-sodium manufactured as described in Example 1; 15.0 g Lutrol E 400® (polyethylene glycol 400); 10.0 g liquid paraffin; 23.0 g Lutrol F 127® (poloxamer 407); QS (to 100 g) purified water.

The topical preparation is prepared as follows: LMWH-sodium is dissolved in water. Lutrol E 400 and liquid paraffin are added. The mixture is stirred and cooled to 6° C. Lutrol F 127 is added slowly to the mixture and the mixture is stirred until dissolved. The resulting mixture is heated to room temperature when the air bubbles escape.

We claim:

1. A method of inducing hair growth in a subject, the method comprising:

(a) identifying a subject in need of hair growth; and (b) topically administering to the subject a composition comprising a low molecular weight heparin (LMWH) preparation, wherein one or more of the polysaccharides of the LMWH preparation have a 2,5-anhydromannitol residue at the reducing end, and a molecular weight distribution such that 10-50% of the polysaccharides of the LMWH preparation have a molecular weight less than 3000 Da; 40-65% of the polysaccharides of the LMWH preparation have a molecular weight between 3000-8000 Da; and 5-30% of the polysaccharides of the LMWH preparation have a molecular weight greater than 8000 Da; and wherein the preparation consists essentially of polysaccharides of Formula I:

$[U_w\text{—}H_{x,y,z}]_m\text{~}[U_G\text{—}H_{x,y,z}]_n$ wherein U indicates a uronic acid residue and H indicates a hexosamine residue; wherein m and n are integers such that m=4-16, and n=1-4; w=–2OS or –2OH; x=—NS or —N-acetylcysteine (NAc); y=–3OS or –3OH; z=–6OS or –6OH;

and $U_G=$

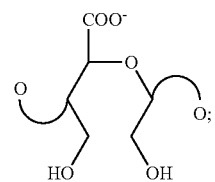

wherein the symbol ~ indicates that the units marked m and n are distributed along the polysaccharide chain and are not necessarily in sequence, wherein w, x, y, and z are each the same or different on each unit marked m, and wherein x, y, and z are each the same or different on each unit marked n; and wherein the LMWH has one or more of the following properties (c)-(e):

(c) anti-Xa activity and anti-IIa activity each less than 50 IU/mg;
(d) less than 50% glycol split uronic acid residues;
(e) weight average molecular weight of between 3,500 and 8,000 Da; and optionally has one or more of the following properties (f)-(i):
(f) greater than 40% $U_{2S}H_{NS,6S}$ disaccharide residues;
(g) degree of desulfation less than 40%;
(h) no more than 3 glycol split uronic acid residues ($U_G$) per polysaccharide chain; and
(i) polydispersity of about 1.2 to 1.7.

2. The method of claim 1, wherein the hair is selected from the group consisting of scalp hair, facial hair, body hair, eyelashes and eyebrows.

3. The method of claim 1, further comprising a step of assessing hair growth before the administering step and/or after the administering step.

4. The method of claim 1, wherein the subject has alopecia.

5. The method of claim 1, wherein the subject has a condition selected from the group consisting of androgenic alopecia, alopecia areata, alopecia totalis, alopecia universalis, telogen effluvium, anagen effluvium, traumatic alopecia, mechanical 'traction alopecia' from hairstyling routines, chemical-induced alopecia, heat-induced alopecia, radiation-induced alopecia, chemotherapy-induced alopecia, scarring alopecia, auto-immune disease induced alopecia, disease-related alopecia, medication-induced alopecia and syphilitic alopecia.

6. The method of claim 1, wherein the subject does not have alopecia.

7. The method of claim 1, wherein the composition is administered in combination with a second agent to promote hair growth.

8. The method of claim 1, wherein the composition is administered in combination with finasteride or minoxidil.

9. The method of claim 1, wherein the composition is administered in combination with one or more agent selected from the group consisting of agents to promote hair growth, vitamins, hydroxy acids, chemical or physical sunscreens, antioxidants, retinoids, progesterones, hair darkening or coloring agents, hair moisturizing agents, and peptides.

10. The method of claim 1, wherein the composition is formulated as a lotion, cream, serum, spray, mousse, aerosol, emulsion, cake, ointment, gel, paste, patch, pencil, towelette, mask, stick, foam, elixir, or concentrate.

11. The method of claim 1, wherein the composition further comprises an agent selected from the group consisting of a lathering surfactant, a moisturizer, an anti-dandruff agent, a second agent to promote hair growth, a vitamin, a hydroxy acid, a chemical or physical sunscreen, an antioxidant, a retinoid, a progesterone, a hair darkening or coloring agent, a hair moisturizing agent, and a peptide.

12. A topical formulation comprising a LMWH preparation, wherein the formulation is a shampoo, a cream, a lotion, a foam, a gel, a serum, a spray, a mousse, an aerosol, an emulsion, a cake, an ointment, a paste, a patch, a pencil, a towelette, a mask, a stick, an elixir, or a concentrate, and wherein one or more of the polysaccharides of the LMWH preparation have a 2,5-anhydromannitol residue at the reducing end, and a molecular weight distribution such that 10-50% of the polysaccharides of the LMWH preparation have a molecular weight less than 3000 Da; 40-65% of the polysaccharides of the LMWH preparation have a molecular weight between 3000-8000 Da; and 5-30% of the polysaccharides of the LMWH preparation have a molecular weight greater than 8000 Da; and wherein the preparation consists essentially of polysaccharides of Formula I: $[U_w—H_{x,y,z}]_m\sim[U_G—H_{x,y,z}]_n$ wherein U indicates a uronic acid residue and H indicates a hexosamine residue; wherein m and n are integers such that m=4-16, and n=1-4; w=-2OS or -2OH; x=—NS or —N-acetylcysteine (NAc); y=-3OS or -3OH; z=-6OS or -6OH;

and $U_G=$

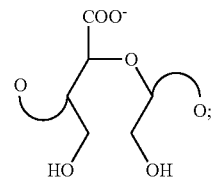

wherein the symbol ~ indicates that the units marked m and n are distributed along the polysaccharide chain and are not necessarily in sequence, wherein w, x, y, and z are each the same or different on each unit marked m, and wherein x, y, and z are each the same or different on each unit marked n, and wherein the LMWH has one or more of the following properties (a)-(c):

(a) anti-Xa activity and anti-IIa activity each less than 50 IU/mg;
(b) less than 50% glycol split uronic acid residues;
(c) weight average molecular weight of between 3,500 and 8,000 Da; and optionally has one or more of the following properties (d)-(g):
(d) greater than 40% U2SHNS,6S disaccharide residues;
(e) degree of desulfation less than 40%;
(f) no more than 3 glycol split uronic acid residues (UG) per polysaccharide chain; and
(g) polydispersity of about 1.2 to 1.7.

13. The topical formulation of claim 12, further comprising an agent selected from the group consisting off a second agent to promote hair growth, a lathering surfactant, a moisturizer, an anti-dandruff agent, a vitamin, a hydroxy acid, a chemical or physical sunscreen, an antioxidant, a retinoid, a progesterone, a hair darkening or coloring agent, a hair moisturizing agent, a fragrance, a wax, an oil, and a peptide.

14. A pharmaceutical, veterinary or cosmetic topical composition, packaged and identified for use in a method of inducing hair growth in a subject, wherein the composition comprises a LMWH preparation, wherein one or more of the polysaccharides of the LMWH preparation have a 2,5-anhydromannitol residue at the reducing end, and a molecular weight distribution such that 10-50% of the polysaccharides of the LMWH preparation have a molecular weight less than 3000 Da; 40-65% of the polysaccharides of the LMWH preparation have a molecular weight between 3000-8000 Da; and 5-30% of the polysaccharides of the LMWH preparation have a molecular weight greater than 8000 Da; and wherein the preparation consists essentially of a polysaccharide of Formula I: $[U_w—H_{x,y,z}]_m\sim[U_G—H_{x,y,z}]_n$ wherein U indicates a uronic acid residue and H indicates a hexosamine residue; wherein m and n are integers such that m=4-16, and n=1-4; w=-2OS or -2OH; x=—NS or —N-acetylcysteine (NAc); y=-3OS or -3OH; z=-6OS or -6OH;

and $U_G=$

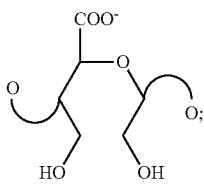

wherein the symbol ~ indicates that the units marked m and n are distributed along the polysaccharide chain and are not necessarily in sequence, wherein w, x, y, and z are each the same or different on each unit marked m, and wherein x, y, and z are each the same or different on each unit marked n, and wherein the LMWH has one or more of the following properties (a)-(c):
(a) anti-Xa activity and anti-IIa activity each less than 50 IU/mg;
(b) less than 50% glycol split uronic acid residues;
(c) weight average molecular weight of between 3,500 and 8,000; and optionally has one or more of the following properties (d)-(g):
(d) greater than 40% U2SHNS,6S disaccharide residues;
(e) degree of desulfation less than 40%;
(f) no more than 3 glycol split uronic acid residues (UG) per polysaccharide chain; and
(g) polydispersity of about 1.2 to 1.7.

15. The method of claim 1, wherein the LMWH preparation has an anti-Xa activity and anti-IIa activity each less than 20 IU/mg.

16. The method of claim 1, wherein the LMWH preparation has an anti-Xa activity and anti-IIa activity each less than 10 IU/mg.

17. The method of claim 1, wherein the LMWH preparation has an anti-Xa activity and anti-IIa activity each less than 5 IU/mg.

18. The method of claim 1, wherein the LMWH preparation has a molecular weight distribution such that 10-40% of the polysaccharides of the LMWH preparation have a molecular weight less than 3000 Da.

19. The method of claim 1, wherein the LMWH preparation has a molecular weight distribution such that 45-65% of the polysaccharides of the LMWH preparation have a molecular weight between 3000-8000 Da.

20. The method of claim 1, wherein the LMWH preparation has a molecular weight distribution such that 15-30% of the polysaccharides of the LMWH preparation have a molecular weight greater than 8000 Da.

21. The method of claim 5, wherein the auto-immune disease induced alopecia is from discoid lupus erythematosus or chronic cutaneous lupus erythematosus.

22. The method of claim 5, wherein the disease-related alopecia is from hyperthyroidism or hypothyroidism or an iron deficiency.

23. The method of claim 5, wherein the medication-induced alopecia is induced by antibiotics, antifungal drugs, antidepressants, anticonvulsants, anticoagulants, or non-steroidal anti-inflammatoeies (NSAIDs).

24. The formulation of claim 12, wherein the LMWH preparation has an anti-Xa activity and anti-IIa activity each less than 20 IU/mg.

25. The formulation of claim 12, wherein the LMWH preparation has an anti-Xa activity and anti-IIa activity each less than 10 IU/mg.

26. The formulation of claim 12, wherein the LMWH preparation has an anti-Xa activity and anti-IIa activity each less than 5 IU/mg.

27. The formulation of claim 12, wherein the LMWH preparation has a molecular weight distribution such that 10-40% of the polysaccharides of the LMWH preparation have a molecular weight less than 3000 Da.

28. The formulation of claim 12, wherein the LMWH preparation has a molecular weight distribution such that 45-65% of the polysaccharides of the LMWH preparation have a molecular weight between 3000-8000 Da.

29. The formulation of claim 12, wherein the LMWH preparation has a molecular weight distribution such that 15-30% of the polysaccharides of the LMWH preparation have a molecular weight greater than 8000 Da.

30. The composition of claim 14, wherein the LMWH preparation has an anti-Xa activity and anti-IIa activity each less than 20 IU/mg.

31. The composition of claim 14, wherein the LMWH preparation has an anti-Xa activity and anti-IIa activity each less than 10 IU/mg.

32. The composition of claim 14, wherein the LMWH preparation has an anti-Xa activity and anti-IIa activity each less than 5 IU/mg.

33. The composition of claim 14, wherein the LMWH preparation has a molecular weight distribution such that 10-40% of the polysaccharides of the LMWH preparation have a molecular weight less than 3000 Da.

34. The composition of claim 14, wherein the LMWH preparation has a molecular weight distribution such that 45-65% of the polysaccharides of the LMWH preparation have a molecular weight between 3000-8000 Da.

35. The composition of claim 14, wherein the LMWH preparation has a molecular weight distribution such that 15-30% of the polysaccharides of the LMWH preparation have a molecular weight greater than 8000 Da.

36. The method of claim 1, wherein the LMWH preparation has glycol split uronic acid residues.

37. The formulation of claim 12, wherein the LMWH preparation has glycol split uronic acid residues.

38. The composition of claim 14, wherein the LMWH preparation has glycol split uronic acid residues.

* * * * *